(12) United States Patent
Toemmeraas et al.

(10) Patent No.: US 8,202,986 B2
(45) Date of Patent: Jun. 19, 2012

(54) BRANCHED HYALURONIC ACID AND METHOD OF MANUFACTURE

(75) Inventors: Kristoffer Toemmeraas, Malmo (SE); Khadija Schwach-Abdellaoui, Frederiksberg (DK)

(73) Assignee: Novozymes Biopolymer A|S, Bagsvaerd (DK)

( * ) Notice: Subject to any disclaimer, the term of this patent is extended or adjusted under 35 U.S.C. 154(b) by 448 days.

(21) Appl. No.: 12/375,425

(22) PCT Filed: Jul. 13, 2007

(86) PCT No.: PCT/DK2007/000358
§ 371 (c)(1),
(2), (4) Date: Jan. 28, 2009

(87) PCT Pub. No.: WO2008/014787
PCT Pub. Date: Feb. 7, 2008

(65) Prior Publication Data
US 2009/0312283 A1 Dec. 17, 2009

Related U.S. Application Data

(60) Provisional application No. 60/836,251, filed on Aug. 7, 2006.

(30) Foreign Application Priority Data

Aug. 4, 2006 (DK) ................. 2006 01034

(51) Int. Cl.
*C08B 37/00* (2006.01)

(52) U.S. Cl. ...................... 536/55.3; 536/55.2

(58) Field of Classification Search ........................ None
See application file for complete search history.

(56) References Cited

U.S. PATENT DOCUMENTS 5,510,121 A * 4/1996 Rhee et al. ................ 424/520
6,703,444 B2 * 3/2004 Zhao et al. ................ 525/61

FOREIGN PATENT DOCUMENTS

| WO | WO 02/18450 | 3/2002 |
| WO | WO 2004/022603 | 3/2004 |
| WO | WO 2004/035629 | 4/2004 |

OTHER PUBLICATIONS

Cho, K. et al "Rlease of ciprofloxacin frm poloxamer-graft-hyaluronic acid gels in vitro" Int. J. Pharm. (2003) vol. 260, pp. 83-91.*
Assayama et al., Bioconjugate Chem., vol. 9, pp. 476-481 (1998).
Laurent et al., The FASEB Journal, vol. 6, pp. 2397-2404 (1992).
Toole, Cell Biology of the Extracellular Matrix, pp. 305-341 (1991).
Tømmerass et al., Carbohydate Research, vol. 337, pp. 2455-2462 (2002).
Crescenzi et al., Biopolymers, vol. 64, pp. 86-94 (2002).

* cited by examiner

*Primary Examiner* — Leigh Maier
(74) *Attorney, Agent, or Firm* — Jason I. Garbell

(57) ABSTRACT

A branched hyaluronic acid, wherein the linear backbone comprises hyaluronic acid in which one or more N-Acetyl-Glucosamine has been deacetylated to Glucosamine, with branching sidechain(s) covalently linked to the primary amine(s) of said deacetylated Glucosamine thus forming a secondary amine(s); a precursor for producing said branched hyaluronic acid; and a method for producing said branching hyaluronic acid.

4 Claims, 1 Drawing Sheet

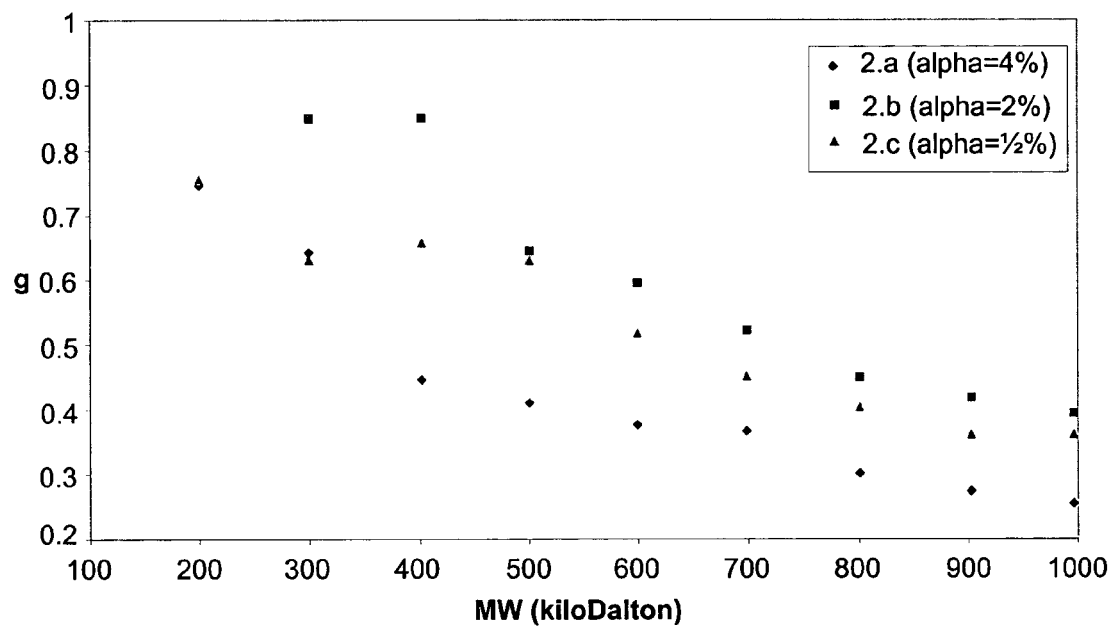

BRANCHED HYALURONIC ACID AND METHOD OF MANUFACTURE

CROSS-REFERENCE TO RELATED APPLICATIONS

This application is a 35 U.S.C. 371 national application of PCT/DK2007/000358 filed Jul. 13, 2007, which claims priority or the benefit under 35 U.S.C. 119 of Danish application no. PA 2006 01034 filed on Aug. 4, 2006 and U.S. provisional application No. 60/836,251 filed on Aug. 7, 2006, the contents of which are fully incorporated herein by reference.

FIELD OF THE INVENTION

The present invention relates to the branching of deacetylated hyaluronic acid (deHA) by reductive alkylation, to the branched hyaluronic acid as such, and to their applications and uses, particularly in the cosmetics and biomedical industries.

BACKGROUND OF THE INVENTION

The most abundant heteropolysaccharides of the body are the glycosaminoglycans. Glycosaminoglycans are unbranched carbohydrate polymers, consisting of repeating disaccharide units (only keratan sulphate is branched in the core region of the carbohydrate). The disaccharide units generally comprise, as a first saccharide unit, one of two modified sugars—N-acetylgalactosamine (GalNAc) or N-acetylglucosamine (GlcNAc). The second unit is usually an uronic acid, such as glucuronic acid (GlcUA) or iduronate.

Glycosaminoglycans are negatively charged molecules, and have an extended conformation that imparts high viscosity when in solution. Glycosaminoglycans are located primarily on the surface of cells or in the extracellular matrix. Glycosaminoglycans also have low compressibility in solution and, as a result, are ideal as a physiological lubricating fluid, e.g., joints. The rigidity of glycosaminoglycans provides structural integrity to cells and provides passageways between cells, allowing for cell migration. The glycosaminoglycans of highest physiological importance are hyaluronan, chondroitin sulfate, heparin, heparan sulfate, dermatan sulfate, and keratan sulfate. Most glycosaminoglycans bind covalently to a proteoglycan core protein through specific oligosaccharide structures. Hyaluronan forms large aggregates with certain proteoglycans, but is an exception as free carbohydrate chains form non-covalent complexes with proteoglycans.

Numerous roles of hyaluronan in the body have been identified (see, Laurent T. C. and Fraser J. R. E., 1992, FASEB J. 6: 2397-2404; and Toole B. P., 1991, "Proteoglycans and hyaluronan in morphogenesis and differentiation." In: Cell Biology of the Extracellular Matrix, pp. 305-341, Hay E. D., ed., Plenum, New York). Hyaluronan is present in hyaline cartilage, synovial joint fluid, and skin tissue, both dermis and epidermis. Hyaluronan is also suspected of having a role in numerous physiological functions, such as adhesion, development, cell motility, cancer, angiogenesis, and wound healing. Due to the unique physical and biological properties of hyaluronan, it is employed in eye and joint surgery and is being evaluated in other medical procedures.

The terms "hyaluronan" or "hyaluronic acid" are used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

HA plays an important role in the biological organism, as a mechanical support for the cells of many tissues, such as the skin, tendons, muscles and cartilage, it is a main component of the intercellular matrix. HA also plays other important parts in the biological processes, such as the moistening of tissues, and lubrication.

HA may be extracted from the above mentioned natural tissues, although today it is preferred to prepare it by microbiological methods to minimize the potential risk of transferring infectious agents, and to increase product uniformity, quality and availability.

HA and its various molecular size fractions and the respective salts thereof have been used as medicaments, especially in treatment of arthropathies, as an auxiliary and/or substitute agent for natural organs and tissues, especially in ophtalmology and cosmetic surgery, and as agents in cosmetic preparations. Products of hyaluronan have also been developed for use in orthopaedics, rheumatology, and dermatology.

HA may also be used as an additive for various polymeric materials used for sanitary and surgical articles, such as polyurethanes, polyesters etc. with the effect of rendering these materials biocompatible.

De-N-acetylation of HA with hydrazine has been described in the literature (Crescenzi et al. (2002) New cross-linked and sulfated derivatives of partially deacetylated hyaluronan: Synthesis and preliminary characterization, Biopolymers 64, 86-94).

Branching of chitosans by reductive HONO degradation and reductive N-alkylation has been described (Tømmeraas et al. (2002) Carbohydrate Research 337, 2455-2462).

SUMMARY OF THE INVENTION

There is a need to develop novel derivatives of biologically compatible biopolymers with desirable properties, for instance, improved visco-elastic properties compared to linear HA, e.g., less sensible to shear thinning or changes in ionic strength, or lower viscosity than linear HA of same MW. These properties are believed to be of value in biomechanical implants and in advanced cosmetic, biomedical and pharmaceutical formulations. Other properties of interest are the improved ability to stabilize foam and the ability to blend with non-hydrophilic materials, such as is used typically in cosmetics products.

In a first aspect, the present invention provides a branched hyaluronic acid, wherein the linear backbone comprises hyaluronic acid in which one or more N-Acetyl-Glucosamine has been deacetylated to Glucosamine, with branching sidechain(s) covalently linked to the primary amine(s) of said deacetylated Glucosamine thus forming a secondary amine(s).

A second aspect of the invention relates to a precursor or intermedia molecule that enters into the method of the third aspect, namely a partially or fully deacetylated hyaluronic acid (dHA), wherein one or more N-Acetyl-Glucosamine has been deacetylated to Glucosamine.

In a third aspect, the invention provides a method for producing a branched hyaluronic acid, the method comprising the steps of:
a) providing a linear hyaluronic acid backbone, wherein one or more N-Acetyl-Glucosamine has been deacetylated to Glucosamine; and
b) reacting a biocompatible polymer comprising at least one free reducing aldehyde group with the primary amine(s) of the one or more Glucosamine of (a) by reductive N-alkylation; to form a branched hyaluronic acid.

In a fourth aspect, the invention relates to a composition comprising a branched hyaluronic acid as defined in the first aspect, and an active ingredient, preferably the active ingredient is a pharmacologically active agent.

A fifth aspect of the invention relates to a pharmaceutical composition comprising an effective amount of a branched hyaluronic acid as defined in the first aspect, together with a pharmaceutically acceptable carrier, excipient or diluent.

A sixth aspect relates to a pharmaceutical composition comprising an effective amount of a branched hyaluronic acid as defined in the first aspect as a vehicle, together with a pharmacologically active agent.

A seventh aspect relates to a cosmetic article comprising as an active ingredient an effective amount of a branched hyaluronic acid as defined in the first aspect or a composition as defined in any of the second, third, or fourth aspects.

In an eighth aspect, the invention relates to a sanitary, medical or surgical article comprising a branched hyaluronic acid as defined in the first aspect or a composition as defined in any of the second, third, or fourth aspects, preferably the article is a diaper, a sanitary towel, a surgical sponge, a wound healing sponge, or a part comprised in a band aid or other wound dressing material.

An important aspect relates to a medicament capsule or microcapsule comprising a branched hyaluronic acid as defined in the first aspect or a composition as defined in any of the fourth to sixth aspects.

Final aspects of the invention relate to methods of performing procedures in ophtalmology, in the treatment of osteoarthritis or cancer, of treating a wound, of performing dermal or transdermal administration of a pharmacologically active agent, or dermal administration of a cosmetic, the improvement which comprises the use of a branched hyaluronic acid as defined in the first aspect, or a composition as defined in any of the third to sixth aspects.

A number of aspects relate to uses of a branched hyaluronic acid as defined in any of the first aspects or a composition as defined in any of the fourth to sixth aspects for the manufacture of a medicament for the treatment of osteoarthritis, cancer, the manufacture of a medicament for an ophtalmological treatment, the manufacture of a medicament for the treatment of a wound, the manufacture of a medicament for angiogenesis, or the manufacture of a moisturizer.

BRIEF DESCRIPTION OF DRAWINGS

FIG. 1 shows a plot of the contraction factor 'g' as function of molecular weight of the hyaluronic acid ($g=(R_{g,branched})^2/(R_{g,linear})^2$). A g-value below 1 indicates branching of the polymer. As can be seen in the FIGURE, the contraction factor increases with increasing molecular weight, thus confirming the preparation of branched HA. Samples 2.a, 2.b and 2.c correspond to samples A, B and C of Example 2 after the branching reaction has been carried out.

DETAILED DESCRIPTION OF THE INVENTION

Hyaluronic Acid

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein to describe the molecule as such, as well as any kind of salt thereof.

Rooster combs are a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP0694616 discloses fermentation processes using an improved strain of *Streptococcus zooepidemicus* with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive *Bacillus* host.

Hyaluronan synthases have been described from vertebrates, bacterial pathogens, and algal viruses (DeAngelis, P. L., 1999, *Cell. Mol. Life Sci.* 56: 670-682). WO 99/23227 discloses a Group I hyaluronate synthase from *Streptococcus equisimilis*. WO 99/51265 and WO 00/27437 describe a Group II hyaluronate synthase from *Pasturella multocida*. Ferretti et al. disclose the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (*Proc. Natl. Acad. Sci. USA.* 98, 4658-4663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as spray drying.

The first aspect of the invention relates to a branched hyaluronic acid, wherein the linear backbone comprises hyaluronic acid in which one or more N-Acetyl-Glucosamine has been deacetylated to Glucosamine, with branching sidechain(s) covalently linked to the primary amine(s) of said deacetylated Glucosamine thus forming a secondary amine(s).

In a preferred embodiment the branching sidechain(s) comprise a biocompatible polymer which preferably comprises hyaluronic acid.

The second aspect of the invention relates to an intermediary or precursor molecule necessary for the manufacture of the branched HA of the first aspect in the method of the third aspect, which is a partially or fully deacetylated hyaluronic acid (dHA), wherein one or more N-Acetyl-Glucosamine has been deacetylated to Glucosamine.

Preferably the one or more N-Acetyl-Glucosamine has been deacetylated by chemical and/or enzymatic treatment, for instance by using hydrazine monohydrate together with hydrazine sulphate, or by using an enzyme having HA deacetylase activity.

A preferred embodiment relates to the dHA of the second aspect, wherein 50% or less of the N-Acetyl-Glucosamines in the linear hyaluronic acid backbone have been deacetylated to Glucosamine, preferably 40% or less, more preferably 30% or less, still more preferably 20% or less, 10% or less, or most preferably 5% or less of the N-Acetyl-Glucosamines in the linear backbone have been deacetylated to Glucosamine.

Another preferred embodiment relates to the dHA of the second aspect, which has an average molecular weight in the range of 10-3,000 kiloDalton, preferably 20-2,000 kDa, and most preferably 20-1,000 kDa, or even smaller, such as 20-900 kDa, 20-800 kDa, 20-700 kDa, 20-600 kDa, 20-500 kDa, 20-400 kDa, 20-300 kDa, 20-200 kDa, or 20-100 kDa.

Molecular Weight

The level of hyaluronic acid may be determined according to the modified carbazole method (Bitter and Muir, 1962, *Anal Biochem.* 4: 330-334). Moreover, the average molecular weight of the hyaluronic acid may be determined using standard methods in the art, such as those described by Ueno et al., 1988, *Chem. Pharm. Bull.* 36, 4971-4975; Wyatt, 1993, *Anal. Chim. Acta* 272: 1-40; and Wyatt Technologies, 1999, "Light Scattering University DAWN Course Manual" and "DAWN EOS Manual" Wyatt Technology Corporation, Santa Barbara, Calif.

It may be advantageous in some instances to first reduce the average molecular weight of the linear hyaluronic acid backbone or salts thereof. For instance, it has been stated by several manufacturers of so-called low-molecular weight fractions of hyaluronic acid, that it is capable of penetrating the skin barrier to reestablish the natural content of hyaluronic acid in the skin, therefore such fractions are particularly suitable for cosmetic compositions sold as anti-skin-ageing and anti-wrinkle agents. For food applications, low MW hyaluronic acid has been shown to penetrate the gastrointestinal barrier, thereby increasing its bioavailability. Finally, low MW hyaluronic acid exhibits anti-inflammatory effect and has potential applications in the treatment of inflammatory diseases. A reduction of the average molecular weight of a hyaluronic acid or derivative or salt thereof may be achieved by standard methods in the art, such as, simple heat treatment, enzymatic degradation, ultrasound sonication, or acid hydrolysis. See, e.g., U.S. Pat. No. 6,020,484, which describes an ultrasonication technique of HA including NaOCl as additive, and T. Miyazaki et al. (2001) Polymer Degradation and Stability, 74: 77-85.

The third aspect of the invention relates to a method for producing a branched hyaluronic acid, the method comprising the steps of:
a) providing a linear hyaluronic acid backbone, wherein one or more N-Acetyl-Glucosamine has been deacetylated to Glucosamine; and
b) reacting a biocompatible polymer comprising at least one free reducing aldehyde group with the primary amine(s) of the one or more Glucosamine of (a) by reductive N-alkylation; to form a branched hyaluronic acid.

Preferably in the method of the third aspect 50% or less of the N-Acetyl-Glucosamines in the linear hyaluronic acid backbone have been deacetylated to Glucosamine, preferably 40% or less, more preferably 30% or less, still more preferably 20% or less, 10% or less, or most preferably 5% or less of the N-Acetyl-Glucosamines in the linear backbone have been deacetylated to Glucosamine.

In a preferred embodiment of the third aspect the linear hyaluronic acid backbone has an average molecular weight in the range of 10-3,000 kiloDalton, preferably 20-2,000 kDa, and most preferably 20-1,000 kDa, or even smaller, such as 20-900 kDa, 20-800 kDa, 20-700 kDa, 20-600 kDa, 20-500 kDa, 20-400 kDa, 20-300 kDa, 20-200 kDa, or 20-100 kDa.

Biocompatible polymers are well-known in the art, and encompasses all kinds of polymers, both naturally produced or synthetically manufactured, which are capable of being degraded and metabolized by an organism, such as a human, without any toxic or unhealthy effects.

Another preferred embodiment relates to the method of the third aspect, wherein the reductive N-alkylation reaction is done in the presence of Sodium Cyanoborohydride, NaCNBH$_3$, preferably at a pH value in the range of 4-10, preferably 5-9, more preferably 6-8, and most preferably at approximately 7.

Other Ingredients

In a preferred embodiment, the compositions comprising a branched HA of the invention may also comprise other ingredients, preferably one or more active ingredient, preferably one or more pharmacologically active substance, and also preferably a water-soluble excipient, such as lactose.

Non-limiting examples of an active ingredient or pharmacologically active substance which may be used in the present invention include protein and/or peptide drugs, such as, human growth hormone, bovine growth hormone, porcine growth hormone, growth homorne releasing hormone/peptide, granulocyte-colony stimulating factor, granulocyte macrophage-colony stimulating factor, macrophage-colony stimulating factor, erythropoietin, bone morphogenic protein, interferon or derivative thereof, insulin or derivative thereof, atriopeptin-III, monoclonal antibody, tumor necrosis factor, macrophage activating factor, interleukin, tumor degenerating factor, insulin-like growth factor, epidermal growth factor, tissue plasminogen activator, factor IIV, factor IIIV, and urokinase.

A water-soluble excipient may be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Several aspects of the invention relate to various compositions and pharmaceuticals comprising, among other constituents, an effective amount of the product as defined in the first aspect, and an active ingredient, preferably the active ingredient is a pharmacologically active agent; a pharmaceutically acceptable carrier, excipient or diluent, preferably a water-soluble excipient, and most preferably lactose.

In addition, aspects of the invention relate to articles comprising a branched HA as defined in the first aspect or a composition as defined in the aspects and embodiments above, e.g., a cosmetic article, a sanitary article, a medical or surgical article. In a final aspect the invention relates to a medicament capsule or microcapsule comprising a product as defined in the first aspect or a composition as defined in other aspects and embodiments of the invention.

EXAMPLES

Example 1

Preparation of Deacetylated HA

HA (6.0 g) was dissolved in hydrazine monohydrate (300 mL) together with hydrazine sulphate (3.0 g) and left on stirring for 92 hours at 55° C. The resulting product was recovered by precipitation with cold ethanol (350 mL). Saturated aqueous NaCl (5 mL) was added to improve precipitation. The recovered precipitate was washed in fresh ethanol (250 mL) and recovered by centrifugation (3000 g, 10 minutes). The recovered material (780 mg) was found to be deacetylated HA (degree of deacetylation 13%).

Example 2

Preparation of Degraded Deacetylated HA

Deacetylated HA (deHA) prepared as described in example 1 was degraded by nitrous acid using the following procedures: Three samples A, B and C of deHA (100 mg) were dissolved in 1% aqueous acetic acid (6 mL). Nitrous acid (NaNO$_2$) was added according to Table 1. The solutions were left for 4 hours in darkness before pH was adjusted to approximately 7.

TABLE 1

Amounts of nitrous acid added to samples A, B and C
and the resulting number of covalent bonds broken.

| Sample | Amount NaNO$_2$ (mg/100 mg HA) | % bonds broken |
|---|---|---|
| A | 1.38 | 4 |
| B | 0.690 | 2 |
| C | 0.345 | 0.5 |

Example 3

Preparation of Branched HA

The samples A, B and C of degraded deHA prepared in example 2 were branched by reductive alkylation using the following procedure: Sodium Cyanoborohydride, NaCNBH$_3$ (20.41 mg) were added to the pH-adjusted solutions from Example 2. The reactions were left to proceed for 48 hours (stirring) before stopped, and products where recovered by dialysis against deionized water (MWCO 12-14 kDa) followed by freeze drying.

Example 4

Analysis by SEC-MALLS-visc

The branched product-samples 2.a, 2.b, and 2.c prepared in Example 3 (corresponding to samples A, B and C of Example 2) were analysed by size exclusion chromatography with the following on-line detectors: MALLS (multi-angle laser light scattering), RI (refractive index) and visc (intrinsic viscosity detector). This was used to evaluate the conformation and molecular weight of the produced materials, i.e., to see if they were branched. FIG. 1 shows a plot of the contraction factor g as function of molecular weight ($g=(R_{g,branched})^2/(R_{g,linear})^2$). A g-value below 1 indicates branching of the polymer. As can be seen, the contraction factor increases with increasing molecular weight, proving the preparation of branched HA.

Table 2 summarizes the properties of the branched HA samples 2.a, 2.b and 2.c. The parameter 'a' in table 2, is obtained from a plot of log $R_g$ vs. log $M_w$. This parameter gives information about the conformation of the polymer in the solvent used (in general; random coil: 0.5-0.6, stiff rod: 1.0 and sphere: 0.33). For the starting material (regular HA), this value is 0.5-0.6, as expected for a random coil conformation. A value around 0.25 is expected for a randomly hyperbranched polymer, giving a further indication that samples 2.a, 2.b and 2.c are branched products.

TABLE 2

Main characteristics of branched HA samples 2.a, 2.b and 2.c ($M_w$ is the weight-average molecular weight, PDI, the polydispersity index, $R_g$, the z-average radius of gyration, [η] the weight-average intrinsic viscosity and a, the exponent of the equation $R_g \sim M^a$)

| Samples | $M_w$ (kDa) | PDI ($M_w/M_n$) | $R_g$ (nm) | [η] (dL/g) | a ($R_g \sim M^a$) |
|---|---|---|---|---|---|
| 2.a | 131 | 1.89 | 39.3 | 511 | 0.24 |
| 2.b | 199 | 2.04 | 57.9 | 772 | 0.21 |
| 2.c | 273 | 2.15 | 55.7 | 492 | 0.30 |

The invention claimed is:
1. A method for producing a branched hyaluronic acid, comprising the steps of:
   a) providing a linear hyaluronic acid backbone, wherein one or more N-Acetyl-Glucosamine has been deacetylated to Glucosamine; and
   b) reacting a biocompatible polymer comprising hyaluronic acid with the primary amine(s) of the one or more Glucosamine of (a) by reductive N-alkylation; to form a branched hyaluronic acid.
2. The method of claim 1, wherein 50% or less of the N-Acetyl-Glucosamines in the linear hyaluronic acid backbone have been deacetylated to Glucosamine.
3. The method of claim 1, wherein the linear hyaluronic acid backbone has an average molecular weight in the range of 10-3,000 kilopalton.
4. The method of claim 1, wherein the reductive N-alkylation reaction is done in the presence of Sodium Cyanoborohydride, NaCNBH3.

* * * * *

UNITED STATES PATENT AND TRADEMARK OFFICE
CERTIFICATE OF CORRECTION

PATENT NO.        : 8,202,986 B2
APPLICATION NO.   : 12/375425
DATED             : June 19, 2012
INVENTOR(S)       : Tømmeraas et al.

Page 1 of 1

It is certified that error appears in the above-identified patent and that said Letters Patent is hereby corrected as shown below:

Title Page, Item (73) Assignee

Delete "Novozymes Biopolymer AIS, Bagsvaerd (DK)" and insert --Novozymes Biopolymer A/S, Bagsvaerd (DK)--.

In claim 3, line 3 at column 8, line 54, delete "kilopalton" and insert --kilodalton--.

Signed and Sealed this
Second Day of April, 2013

Teresa Stanek Rea
*Acting Director of the United States Patent and Trademark Office*